United States Patent [19]

Krainski, Jr.

[11] 4,332,175

[45] Jun. 1, 1982

[54] COUNTERBALANCE LOADING DEVICE

[75] Inventor: Theodore J. Krainski, Jr., Old Bridge, N.J.

[73] Assignee: Johnson & Johnson, New Brunswick, N.J.

[21] Appl. No.: 149,221

[22] Filed: May 12, 1980

[51] Int. Cl.³ .............................................. G01N 3/10
[52] U.S. Cl. ..................................................... 73/825
[58] Field of Search .................................. 73/825, 818

[56] References Cited

U.S. PATENT DOCUMENTS 2,245,080  6/1941  Pendleton .............................. 73/825
3,413,849  12/1968  Janapol ................................. 73/825

Primary Examiner—Anthony V. Ciarlante
Attorney, Agent, or Firm—Donal B. Tobin

[57] ABSTRACT

A counterbalanced loading device including a compensated main piston cylinder and piston rod operating through a load transfer assembly to apply a desired load to a pressure foot. The weight of the main piston and its associated load transfer assembly is counterbalanced by a separate counterforce piston, commonly driven with the main drive piston through a pneumatic circuit.

7 Claims, 2 Drawing Figures

COUNTERBALANCE LOADING DEVICE

BACKGROUND OF THE INVENTION

The present invention relates to counterbalance loading device and more particularly to a compensated main piston drive device for applying small loads to a test sample which includes a counterbalance piston to compensate for the weight of the main drive piston so that the lower limit of the applied load is not constrained by the weight of the hardware used.

The present invention has found particular application in the field of measuring the absorbency of various absorbent materials of the kind that would be used in disposable diapers, bandages, sanitary napkins, incontinent pads and the like. During use there is often a compression load on such devices, for example a baby might be sitting on the diaper or a bandage might be wound with some tightness about the body. Therefore, when one is testing the absorbency of a particular material, it is useful to place a compression load on the material and to vary the load according to specific time sequences or other parameters. The absorbency data collected under these conditions will more accurately reflect actual use.

When one is actually testing the absorbency of such material in a laboratory, it is useful to be able to load the material with a prescribed load for a prescribed period of time and to record the data automatically. Especially in the laboratory environment, it is useful to be able to quickly and easily change the applied loads and the time sequences without having to waste valuable laboratory time in resetting the test apparatus.

In the past, such tests had been conducted by a laboratory technician who would place a test sample on a flat surface under a pressure plate and then manually place known weights on the pressure plate. The technician observes the sample and measures it thickness at regular time intervals. There is a correlation between the thickness and absorbency of the test sample as pointed out in the testing procedure that is employed by a Gravimetric Absorption Tester, described in U.S. patent application Ser. No. 149,214 filed on the same day as this application by Wesley J. McConnell, and assigned to the same assignee of this application. The said McConnell application is incorporated herein by reference.

If the test sample is small, the weight of the pressure plate may be unimportant. However, for larger samples, for example, three or four inches in diameter, the weight of the pressure plate may significantly effect the lower limit of the applied load. This further inhibits the use of automatic testing procedures.

It would be desirable to have an automatic loading device in which the weight of the pressure plate and the load-applying apparatus is automatically compensated so that the lower limit of applied load is not unreasonably restrained. It would also be desirable to have an automatic loading device which could be automatically programmed to apply a variety of desired loads for a variety of time periods.

SUMMARY OF THE INVENTION

The present invention relates to such an automatically compensated loading device which is also adapted to be automatically programmed to apply a variety of desired loads for a variety of time periods. The loading device includes a housing in which a first cylinder is rigidly supported. This first piston receives pneumatic pressure input from a transducer whose output is controlled by a programmable control unit. The control unit is the subject of a separate patent application Ser. No. 149,216 filed on the same day as this application by the present inventor and assigned to the same assignee of this application. The application for the control unit is incorporated herein by reference.

A first drive piston rides in the first cylinder and applies a desired load to a first piston rod, thence to a load transfer platform which moves freely within the housing. Connected to the load transfer platform is a load cell which is rigidly connected to an output shaft which extends through the housing and is rigidly connected to a pressure plate. Thus the applied load is transferred to the pressure foot. The load cell provides a feedback mechanism to make sure that the actual applied load conforms to the desired input load.

A second compensating cylinder is rigidly affixed to the inside of the housing and receives a second pneumatic input which is applied to a second piston riding in the compensating cylinder. The second piston is rigidly connected to the load transfer platform by a second piston rod which compensates for the weight of the load transfer platform and the parts which are operatively connected to it, namely, the first piston and piston rod, the load cell, output shaft and pressure foot. The pneumatic input to the second cylinder may be calibrated to balance the operative parts of the loading device so that when zero load is applied to the pressure foot, the test sample actually experiences zero load rather than a bias load equal to the weight of the operative parts of the loading device. The loading device also includes a pneumatic input circuit including pressure regulators and a current-to-pressure transducer.

The loading device also includes a linear variable differential transformers (LVDT) to monitor any changes in thickness of the test sample as it absorbs fluid. The sample may either expand or collapse. The body of the LVDT is fixed to the outside of the housing. The core of the LVDT is fixed to part of the load transfer mechanism, for example the load cell, so that as the pressure foot moves with the change in thickness of the test sample, the core of the LVDT will move into or out of the LVDT body to generate a signal representative of the change in thickness.

BRIEF DESCRIPTION OF THE DRAWINGS

These and other features of the present invention will be more readily appreciated from the following detailed description of the preferred embodiments of the invention taken in conjunction with the following drawings in which.

DETAILED DESCRIPTION OF THE PREFERRED EMBODIMENT

Figure 1:
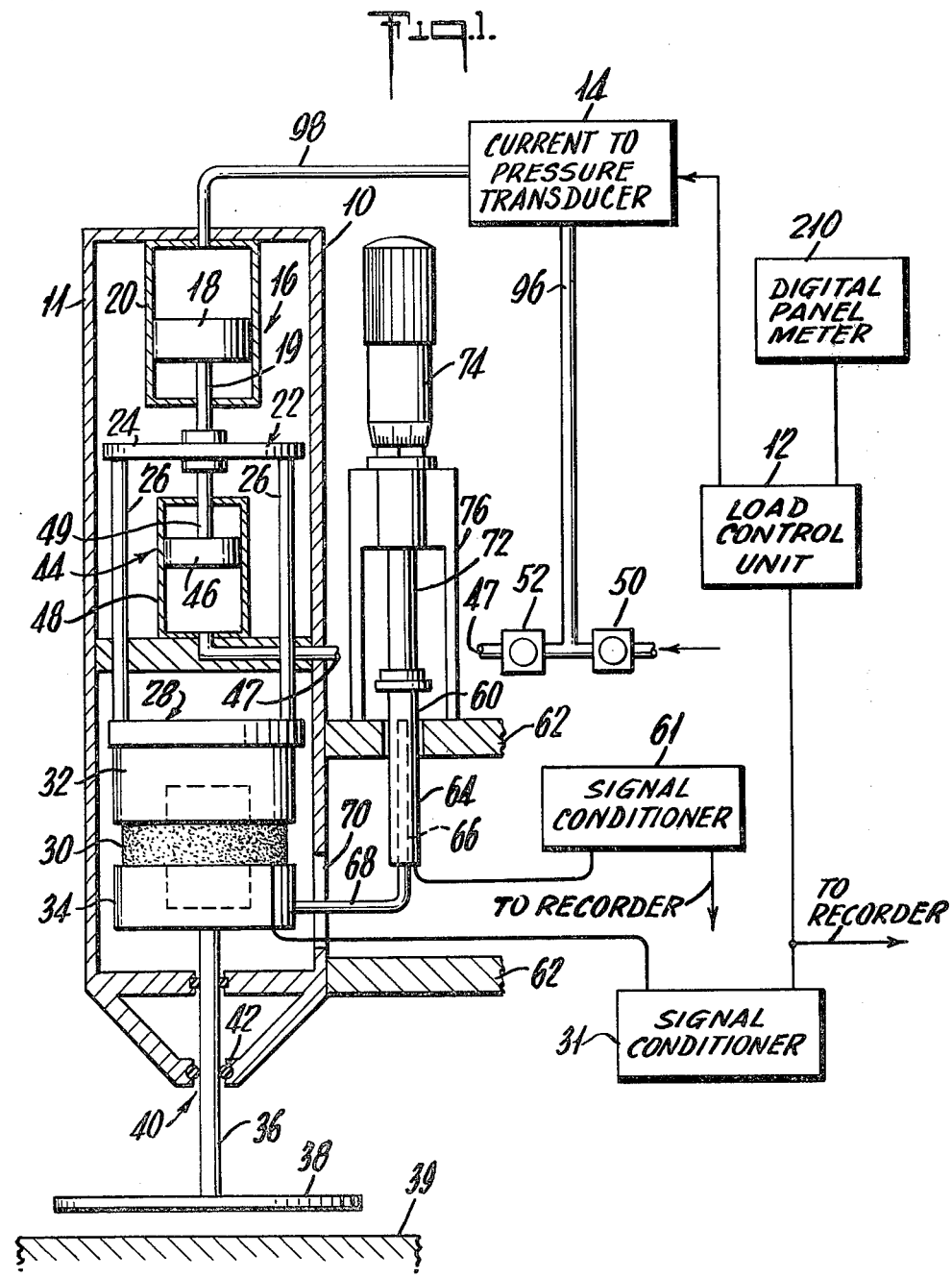
FIG. 1 shows a schematic representation of the loading device is association with which the control apparatus of the present invention is used; and, FIG. 2 shows a schematic representation of a transducer used in association with the apparatus of FIG. 1.

Referring now to FIG. 1, there is shown a sample load device 10 which is controlled by the load control unit 12. Load control unit 12 generates an electrical signal representative of the desired load to be applied to the loading device and transmits that electric signal to a current-to-pressure transducer 14 which converts the electrical signal to a pneumatic output. The pneumatic output is transferred to a first piston actuator 16 comprising a piston 18 moving in cylinder 20, which is rigidly supported on housing 11 of load unit 10. The load applied to the upper surface of piston 18 is transferred through piston rod 19 to load transfer assembly 22 which includes a load transfer platform 24 connected by stiff arms 26 to a load cell assembly 28. Load cell assembly 28 includes a force transducer 30 threaded in plastic mountings 32 and 34, which is in turn rigidly connected to output shaft 36, passing through linear ball bushing 42 in guide 40 and terminating in a pressure foot 38 which abuts the test sample (not shown) resting on base plate 39. Thus, the pneumatic load applied to the top of piston 18 is transmitted through the loading device 10 to pressure foot 38. The load applied by foot 38 to the test sample is measured by load cell 30. Load cell 30 is a standard device generally available from a number of manufacturers and which includes two parallelly aligned mounting plates separated by springs having known spring constants. A transformer body is usually mounted on one plate and a transformer core is mounted on the other. The transformer output varies as the plates move toward or away from each other and the transformer core moves into or out of the transformer body in response to a force applied to the load cell. Since the spring constant of the springs separating the two plates is known, and since the transformer output is directly related to the deflection between the two plates, the load cell can be calibrated to read an applied load. A suitable load cell may be purchased from Schaevits Engineering Company of Camden, New Jersey, Model No. FTA-IT-20. A signal conditioner 31 is used in association with load cell 30 to provide a power supply and to condition the output of load cell 30 to a useful format. The load cell output is directed to signal conditioner 31 and thence to load control unit 12 and to a recording means.

The loads which are meant to be applied to the test samples are necessarily small and, thus, the data can be affected by the weight of the load transfer apparatus itself, including the moving parts of load device 10, i.e., piston 18, piston rod 19, the load transfer assembly 22, load cell 30 and its mountings 32 and 34, output shaft 36 and pressure foot 38. To compensate for the weight of these parts of loading device 10, the loading device 10 includes an offset counterforce system 44, which includes a piston 46 in a cylinder 48 with a piston rod 49 rigidly connected to load transfer platform 24. Piston 48 is supplied with a constant pneumatic pressure through conduit 47 which urges piston 46 in a direction opposite to that of piston 18 so that load transfer assembly 22 is urged upward with sufficient force to counterbalance the weight of the moving parts of loading device 10. The counterforce assembly 44 presses upwardly with a preset force somewhat greater than the weight of the moving portions of the sample loading device 10. The device is then calibrated so that at zero load, piston 16 presses down with a force equal to or less than the counterforce exerted on piston 46. Light weight materials are used in the loading device as much as possible. The pistons are preferably made of graphite and the cylinders preferably made of glass to reduce friction loading within the cylinders.

As shown in FIG. 1, an air supply is introduced into cylinder 48 through two pressure regulators 50 and 52. These pressure regulators can be purchased from Fairchild Industrial Products Division, Winston Salem, North Carolina under Fairchild Pneumatic Pressure Regulator Model 30. Pressure regulator 50 is preferably a 0 to 30 pound pressure regulator which is set to output about 22 pounds per square inch. Pressure regulator 52 is a 0 to 2 pound pressure regulator with an output of about 1.8 pounds per square inch. It can be seen in FIG. 1 that the air pressure supply from the downstream side of pressure regulator 50 is directed to the input serves as the air pressure supply for cylinder 20. Current-to-pressure transducer 14 will be discussed more thoroughly in connection with FIG. 2 further on in the application.

Still referring to FIG. 1, there is shown a linear variable differential transformer (LVDT) 60 rigidly mounted on a support platform 62 which also supports load device 10. LVDT 60 is used to measure the thickness of the test sample placed on base plate 39. Transformer body 64 is adjustably mounted on the stem 72 of a vernier 74, vernier 74 is mounted on support 62 by legs 76.

Transformer core 66 is affixed to mounting 34 of load cell 30 by means of an arm 68 which extends through slot 70 in the housing of load device 10.

As foot 38 moves up and down according to the variation of thickness of the test sample, load cell support 34, arm 68 and transformer core 66 will correspondingly move, causing core 66 to move with respect to transformer body 60, thus causing the transformer output to vary in accordance with the motion of foot 38. This provides a method of measuring the thickness of a sample that is being subjected to a test. The thickness of a test sample can be monitored and displayed on a digital panel meter 210 and/or recorded on a recording means such as a chart recorder. In order to set the foot at a zero thickness above the surface on which a test sample will be placed, the electronic circuit can be engaged and vernier 74 may be adjusted until the thickness on the digital panel meter reads zero.

Figure 2:
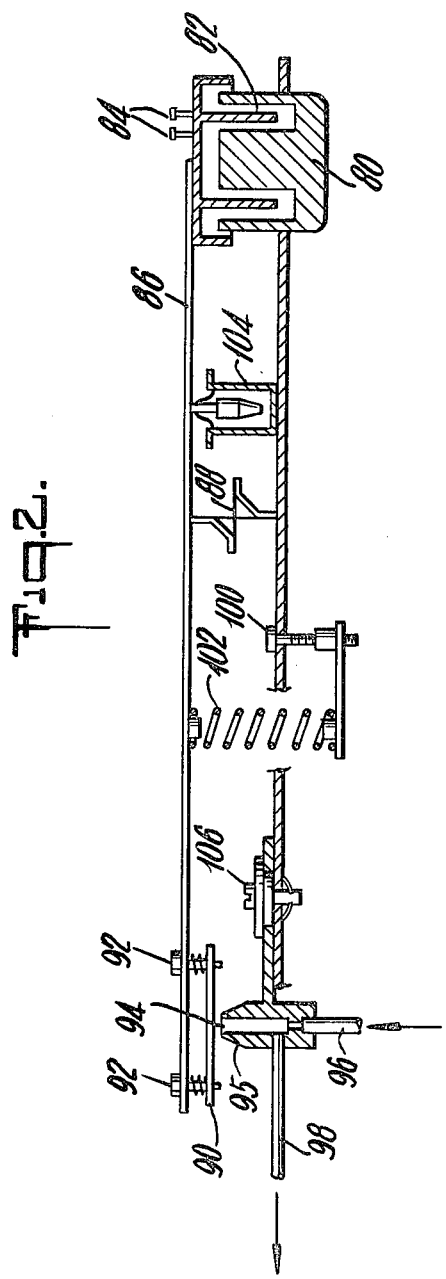

The operation of current-to-pressure transducer 14 will now be described in conjunction with FIG. 2. Current-to-pressure transducer 14 is a force-balance instrument that balances an electromagnetic force against a pneumatic force. Transducer 14 includes a permanent magnet 80 and an electrical coil 82. An input signal current is applied to coil 82 through contacts 84. Coil 82 of transducer 14 is mounted on one end of force lever 86 which pivots on flexure pivot 88. An adjustable baffle 90 is mounted on the other end of lever 86 which may be adjusted by means of spring loaded screws 92. Transducer coil 82 is suspended in the gap of permanent magnet 80. As the current flow through transducer coil 82 increases, the coil moves up out of the gap of magnet 80, raising the coil end of force lever 86 and lowering baffle 90 against orifice 94 of nozzle 95, directing the air supply from input line 96 to output line 98 and into cylinder 20 of load device 10. As the input signal current to the transducer coil decreases, the coil moves down into the gap of magnet 80 and raises baffle 90 out of engagement with nozzle 95 to permit the air supply from input line 96 to vent to the atmosphere, thus reducing the amount of pressure directed through output line 96 into cylinder 20. A zero-adjustment screw 100 is provided to compress zero-adjustment spring 102. Zero adjustment 100 may be adjusted together with pressure regulator 52 to insure that when a "zero" load signal is delivered to transducer 14, that the air in cylinder 44 is sufficient to overcome the air pressure in cylinder 20 and the weight of the moving parts of load unit 10, so that when "zero" load exists foot 38 will automatically rise from base plate 39. Damper 104 is provided. A span adjustment 106 is provided to position nozzle 95 in relation to pivot 88. Span adjustment 106 is provided by a pair of screwdriver adjusted cams which can slide the nozzle axially of force lever 86. Thus current-to-pressure transducer 14 will convert the output of load control unit 12 to a pneumatic output for introducing a load into cylinder 20 which will be delivered through the apparatus of load device 10 to foot 38 and to the test sample. Load cell 30 provides a feedback to load-control unit 12 to insure that the desired applied load is properly adjusted and maintained at the required level and will not drift from that required level.

The operation and construction of load-control unit 12 are described in a separate patent application filed on the same day as this patent application U.S. Pat. Application Ser. No. 144,216 by the same inventor and assigned to the same assignee as this application and is hereby incorporated by reference herein.

Load unit 12 can be programmed to apply a desired load for desired time periods to load device 10. Load unit 12 generates a signal representative of desired load to current-to-pressure transducer 14 which converts the signal to a pneumatic output. When load control unit 12 has completed its programmed instructions it generates a signal to coil 82 of current-to-pressure transducer 14, which completely opens baffle 90 away from nozzle 95 and bleeds off the supply of air to cylinder 20 of load device 10. The air supply directed to cylinder 48 against piston 46 of counterbalance unit 44 is then sufficient to overcome the weight of the moving parts of load unit 10 and raise foot 38. Thus, when load unit 12 has completed its sequence, load unit 12 shuts itself off and raises foot 38.

Thus, the present invention provides a loading device compensated for the weight of the device itself so that the lower limit of the applied load need not be unreasonably constrained. Although the invention has been described as a pneumatic device, it could be hydraulically operated. While this invention has been described in conjunction with certain preferred embodiments, those skilled in the art will appreciate that many changes and modifications may be made to the preferred embodiment without departing from the scope of the invention. Thus, it is not intended that the scope of the invention be limited except as set forth in the following claims.

I claim:

1. Apparatus for applying a load to a test sample comprising:
    a housing;
    a first cylinder rigidly affixed inside said housing and adapted to receive a first supply of fluid under pressure;
    a first piston slidably mounted in said first cylinder and moveable in response to said first pressurized fluid supply;
    a first piston rod connected to said first piston to transmit the force supplied to said first piston out of said first cylinder;
    a load transfer assembly disposed within said housing having a first end rigidly affixed to said first piston rod and having a second end affixed to an output shaft so that said output shaft will move together with said first piston;
    a counterbalance cylinder rigidly affixed within said housing and adapted to receive a second supply of fluid under pressure and having a piston slidably mounted therewithin and moveable in response to said second pressurized fluid supply in a direction opposite to the motion of said first piston;
    a counterbalance piston rod having a first end connected to said counterbalance piston and a second end connected to said load transfer assembly to transmit the force applied to said counterbalance piston to said load transfer assembly to counterbalance the weight of said first piston rod, said first piston, said load transfer assembly and said output shaft.

2. The apparatus of claim 1 further including a load cell having one end affixed to said load transfer assembly and having the other end affixed to said output shaft, said load cell being adapted to provide an output signal representative of the load applied to said output shaft.

3. The apparatus of claim 2 further including a linear variable differential transformer having a body rigidly mounted outside said housing and having a core rigidly mounted to said load cell, said core extending through said housing into the body of said linear variable differential transformer so that as said load cell moves, said transformer core moves with respect to said transformer body to provide an output signal representative of said motion.

4. The apparatus of claim 1 further including a fluid circuit for providing fluid under pressure to said first cylinder and to said counterbalance cylinder and including a first pressure regulator connected in fluid communication between said fluid supply and said first piston; and, a second pressure regulator connected in fluid communication between the output of said first pressure regulator and said counterbalance cylinder, said second pressure regulator being adjustable to provide the desired amount of counterbalance force to said counterbalance piston.

5. The apparatus of claim 4 wherein the fluid circuit is a pneumatic circuit and further including:
    a current-to-pressure transducer connected in series with said first cylinder and operative in response to a control signal to vary the pressure applied to said first cylinder.

6. The apparatus of claim 1 wherein said load transfer assembly includes:
    an upper load transfer platform movably mounted within said housing and extending substantially thereacross and having a first side connected to said first piston and having a second side rigidly connected to said counterbalance piston;
    a lower load transfer platform movably mounted within said housing and extending substantially thereacross;
    a plurality of stiff arms connecting the periphery of said upper and lower load transfer platforms;
    said upper and lower load transfer platforms defining a central space within which said counterbalance cylinder is disposed;
    said stiff arms slidably extending through said counterbalance cylinder mounting.

7. The apparatus of claim 3 further including a vernier rigidly affixed outside said housing and having a stem connected to the body of said linear variable differential transformer so that the relative position of said body with respect to said transformer core can be varied by adjusting the vernier.

* * * * *